United States Patent [19]

Umezawa et al.

[11] 4,370,318
[45] Jan. 25, 1983

[54] BESTATIN-RELATED COMPOUNDS AS IMMUNOPOTENTIATOR

[75] Inventors: Hamao Umezawa; Tomio Takeuchi, both of Tokyo; Takaaki Aoyagi, Fujisawa; Kenji Kawamura, Zama; Shunzo Fukatsu, Tokyo, all of Japan

[73] Assignee: Zaidan Hojin Biseibutsu Kagaku Kenkyu Kai, Japan

[21] Appl. No.: 272,211

[22] Filed: Jun. 10, 1981

[30] Foreign Application Priority Data

Jul. 7, 1980 [JP] Japan ................................. 55/91690
Jul. 7, 1980 [JP] Japan ................................. 55/91691
Jul. 7, 1980 [JP] Japan ................................. 55/91692

[51] Int. Cl.³ ..................... A61K 37/00; A61K 31/16; A61K 31/165
[52] U.S. Cl. .................................. 424/177; 424/320; 424/324; 564/153; 564/158; 564/165; 564/219; 564/360
[58] Field of Search ....................... 424/177, 320, 324; 564/360, 153, 158, 165, 219

[56] References Cited

FOREIGN PATENT DOCUMENTS 2725732 12/1978 Fed. Rep. of Germany ...... 424/177
7622279 7/1976 France ................................. 424/177

OTHER PUBLICATIONS

Y. Iitaka, The Journal of Antibiotics (1976) pp. 102, 103.
H. Suda, et al., The Journal of Antibiotics (1976) pp. 600, 601.
R. Sharma, et al., Journal of the Chemical Society (1979) pp. 875-877.
Takita, et al., Journal of Medicinal Chemistry 1977, vol. 20, No. 4, pp. 510-515.

*Primary Examiner*—Delbert R. Phillips
*Attorney, Agent, or Firm*—Larson and Taylor

[57] ABSTRACT

3-Amino-2-hydroxy-4-phenylbutanoic acid and esters thereof as well as new derivatives thereof which are related to bestatin in their chemical structure are active to enhance the immune response in living animals.

12 Claims, No Drawings

BESTATIN-RELATED COMPOUNDS AS IMMUNOPOTENTIATOR

SUMMARY OF THE INVENTION

This invention relates to new chemical compounds which are related compound of bestatin and which are useful as immunopotentiator for enhancing the immunological response in animals and humans. This invention also includes the production of these new compounds. This invention further relates to uses of these new compounds and their related known compounds as the immunopotentiator.

BACKGROUND OF THE INVENTION

Bestatin is known to have the immunopotentiating properties (see U.S. Pat. No. 4,029,547 and U.S. Pat. No. 4,189,604). Bestatin is (2S, 3R)-3-amino-2-hydroxy-4-phenylbutanoyl-(S)-leucine and has the following structure:

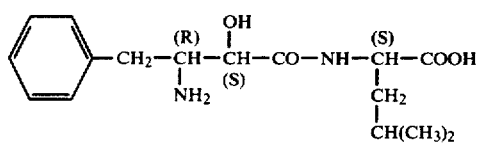

We earlier have chemically synthetized some compounds which are related to bestatin in their chemical structure and which are represented by the following general formula:

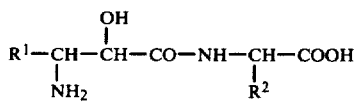

wherein $R^1$ is

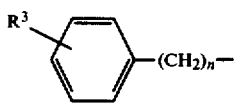

where $R^3$ is hydrogen, chloro, methyl, nitro, hydroxy or amino and n is 0 or 1, and $R^2$ is a (lower)alkyl having 1 to 6 carbon atoms, hydroxy(lower)-alkyl, alkylthioalkyl, carboxamido(lower)alkyl or carboxy(lower)-alkyl, provided that when $R^1$ is benzyl and $R^2$ is isobutyl, the configuration of the compound is (2S,3R,2'R), (2S,3S,2'S) or (2S,3S,2'R) (see U.S. Pat. No. 4,189,604 issued on Feb. 19, 1980). The compounds of the formula (II) are the dipeptides which are physiologically active and inhibit aminopeptidase B, leucine aminopeptidase and Bleomycin hydrolase and enhance the anti-tumor effect of bleomycin.

We have further researched bestatin and its related known compounds, and now we have succeeded to provide further new compounds which are related to bestatin in their chemical structure and which have the aminopeptidase-inhibiting activity and the immunopotentiating activity.

An object of this invention is to provide new compounds which exhibit the immunopotentiating activities. Another object of this invention is to provide processes for the production of these new compounds. Further object is to provide an immunopotentiator comprising these new compounds or their related known compounds. Other objects and utilities of this invention will be clear from the following descriptions.

DETAILED DESCRIPTION OF THE INVENTION

According to a first aspect of this invention, there is provided a new compound of the formula:

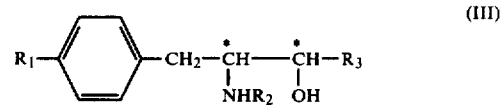

wherein $R_1$ is a hydrogen atom or a hydroxyl group, $R_2$ is a hydrogen atom or an alkanoyl group of 2–7 carbon atoms or an alkoxycarbonyl group of 2–7 carbon atoms, and $R_3$ is selected from the groups:

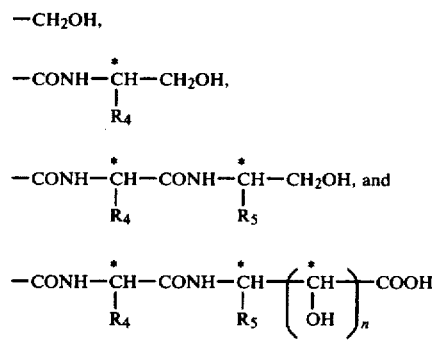

where $R_4$ and $R_5$ may be the same or different from each other and each are an alkyl group of 1–7 carbon atoms, a hydroxyalkyl group of 1–7 carbon atoms, a mercaptoalkyl group of 1–7 carbon atoms, a carboxamidoalkyl group of 2–8 carbon atoms, an aminoalkyl group of 1–7 carbon atoms, a guanidyl-N-alkyl group of 1–7 carbon atoms, an alkylmercaptoalkyl group of 2–7 carbon atoms, a carboxyalkyl group of 2–8 carbon atoms, an aryl group, particularly phenyl, an aralkyl group of 2–8 carbon atoms or a substituted aralkyl group of 2–8 carbon atoms, n is zero or 1, and the asterisk (*) denotes the R-configuration or S-configuration.

The new compound of the formula (III) may be in the form of a pharmaceutically acceptable acid-addition salt or a pharmaceutically acceptable salt (carboxaylate).

According to a preferred embodiment of this invention, there is provided a new compound of the formula:

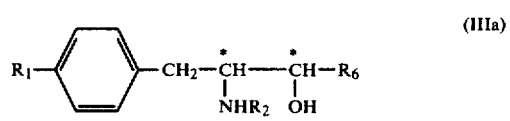

wherein $R_1$ is a hydrogen atom or a hydroxyl group, $R_2$ is a hydrogen atom or an alkanoyl group of 2 to 7 carbon atoms or an alkoxycarbonyl group of 2 to 7 carbon atoms, and $R_6$ is the group:

—CH$_2$OH,

-continued

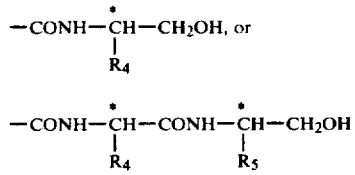

where $R_4$ and $R_5$ are as defined before in respect of the formula (III), and the asterisk (*) each denotes the R-configuration or S-configuration.

Specific examples of the new compound (IIIa) of this invention include the following:

(1) (2S,3R)-3-amino-2-hydroxy-4-phenyl-1-butanol,
(2) ((2S)-2-N-[(2'S,3'R)-3'-amino-2'-hydroxy-4'-phenyl-butanoyl]amino-4-methyl-pentanol,
(3) (2S)-2-N-[(2S,3'R)-3'-N-acetylamino-2'-hydroxy-4'-phenylbutanoyl]amino-4-methyl-pentanol, and
(4) (2S)-2-N-[(2'S,3'R)-3'-amino-2'-hydroxy-4'-phenyl-butanoyl-(S)-leucyl]amino-4-methyl-pentanol.

According to another preferred embodiment of this invention, there is provided a new compound of the formula:

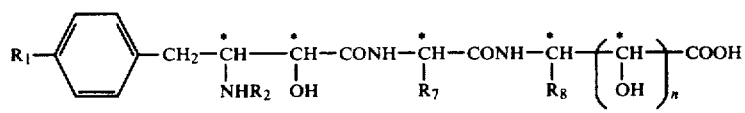
(IIIb)

wherein $R_1$ is a hydrogen atom or a hydroxyl group, $R_2$ is a hydrogen atom or an alkanoyl group of 2 to 7 carbon atoms or an alkoxycarbonyl group of 2 to 7 carbon atoms, and $R_7$ and $R_8$ may be the same or different from each other and each are an alkyl group of 1 to 7 carbon atoms, a hydroxyalkyl group of 1 to 7 carbon atoms, a mercaptoalkyl group of 1 to 7 carbon atom, an aminoalkyl group of 1 to 7 carbon atoms, a guanidyl-N-alkyl group of 1 to 7 carbon atoms, an alkylmercaptoalkyl group, a carboxyalkyl group of 2 to 8 carbon atoms, a carboxamidoalkyl group of 2 to 8 carbon atoms, an aryl group, particularly phenyl group, an aralkyl group, particularly a phenyl($C_1$-$C_4$)alkyl group, especially benzyl, or a substituted aralkyl group, and n is 0 or 1, and the asterisk (*) denotes the R-configuration or S-configuration.

Specific examples of the new compound of the formula (IIIb) of this invention include the following:

(5) (2S,3R)-3-amino-2-hydroxy-4-phenylbutanoyl-(S)-leucyl-(S)-leucine,
(6) (2S,3R)-3-amino-2-hydroxy-4-phenylbutanoyl-(S)-leucyl-(S)-arginine,
(7) (2S,3R)-3-amino-2-hydroxy-4-phenylbutanoyl-(S)-leucyl-(R)-leucine,
(8) (2S,3R)-3-amino-2-hydroxy-4-phenylbutanoyl-(S)-leucyl-(S)-glutamic acid, and
(9) (3R)-N-[(2'S,3'R)-3'-amino-2'-phenylbutanoyl-S-leucyl]amino-(2S)-2-hydroxy-4-phenylbutanoic acid.

According to a further preferred embodiment of this invention, there is provided a new compound of the formula:

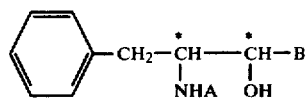
(IIIc)

wherein A is a hydrogen atom or an alkanoyl group of 2 to 5 carbon atoms, especially acetyl and B is the group:

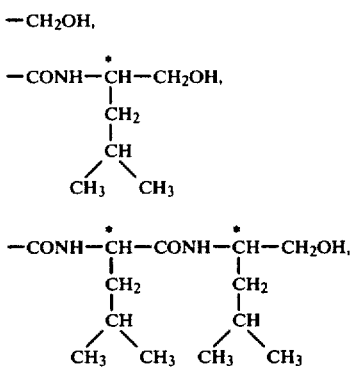

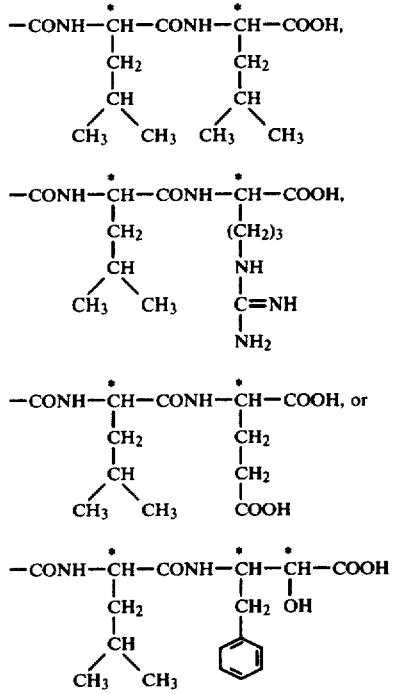

Amongst the new compounds of the general formula (III) according to this invention, the new compound of the formula (IIIa) may be prepared by a process comprising reducing a compound of the formula (IV):

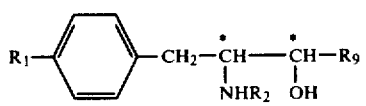

(IV)

wherein $R_1$ is a hydrogen atom or a hydroxyl group as defined above, $R_2$ is a hydrogen atom or an alkanoyl group or alkoxycarbonyl group as defined above, and $R_9$ is the group:

$$-COOR_{10},$$

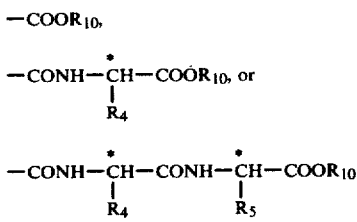

where $R_4$ and $R_5$ are each an alkyl group of 1 to 7 carbon atoms, a hydroxylalkyl group of 1 to 7 carbon atoms, a mercaptoalkyl group of 1 to 7 carbon atoms, a carboxaminoalkyl group of 2 to 8 carbon atoms, an aminoalkyl group of 1 to 7 carbon atoms, a guanidyl-N-alkyl group of 1 to 7 carbon atoms, an alkylmercaptoalkyl group of 2 to 7 carbon atoms, a carboxyalkyl group of 2 to 8 carbon atoms, an aryl group, particularly phenyl, an aralkyl group of 7 to 8 carbon atom, particularly benzyl or a substituted aralkyl group of 7 to 8 carbon atoms; and $R_{10}$ is an alkyl group of 1 to 7 carbon atoms, especially methyl or ethyl or an aralkyl group of 7 to 8 carbon atoms, especially benzyl, and the asterisk (*) denotes the R-configuration or S-configuration, or a protected derivative of the compound (IV) having protected its functional group which should not participate in the reduction, and if necessary, removing the residual protective group from the resulting reduction product in a known manner.

The starting compound (IV) employed in the above process is usually in the form of an alkyl or aralkyl (eg. benzyl) ester (carboxylate) of an amino acid, dipeptide or tripeptide which is corresponding to such compound that the terminal methylol group (—CH₂OH) of the final product to be produced is replaced by an alkyl or aralkyl carboxylate group (—COOR₁₀). When the starting compound (IV) is in the form of an alkyl ester of an amino acid, the latter may be, for instance, the methyl ester of (3R)-N-tert-butoxycarbonylamino-(2S)-hydroxy-4-phenylbutanoic acid which may be prepared by protecting the amino group of (3R)-amino-(2S)-hydroxy-4-phenylbutanoic acid (Journal of Antibiotics, Vol. 29, No. 5, 600–601 (1976)) with the known amino-protective group, tert-butoxycarbonyl group and then esterifying the protected product with diazomethane in ethyl ether. When the compound (IV) is in the form of an alkyl ester of a dipeptide, the latter may be, for instance, the methyl ester of (2S,3R)-3-N-tert-butoxycarbonylamino-4-phenylbutanoyl-(S)-leucine which may be prepared by protecting the amino group of bestatin (U.S. Pat. No. 4,029,547) with tert-butoxycarbonyl group and then esterifying the N-protected bestatin with diazomethane in ethyl ether. When the starting compound (IV) is in the form of an alkyl ester of a tripeptide, the latter may be prepared by condensing in a known manner for the conventional systhesis of peptides an alkyl ester of an appropriate amino acid with N-benzyloxycarbonylbestatin which may, in turn, be produced by reacting bestatin with a benzyloxycarbonylating agent such as benzyloxycarbonyl-p-nitrophenyl ester, benzyloxycarbonyl azide, benzyloxycarbonyl-N-hydroxysuccinimide ester and benzyloxycarbonyl-4,6-dimethyl-2-mercaptopyrimidine in aqueous dioxane, tetrahydrofuran, acetonitrile or dimethylformamide.

In order to produce the new compound (IIIa) from the starting compound (IV), the compound (IV) is reduced in a manner known for the conventional conversion of a lower alkyl carboxylate (ester) into the corresponding alcohol, that is, with a reducing agent which is usually used for this purpose, for example, with sodium borohydride in a lower alkanol, either aqueous or anhydrous, at ambient temperature. After the reduction is completed, removal of the remaining amino-protecting group is carried out by a known deprotecting technique, if necessary. The amino-protecting benzyloxycarbonyl group may be removed by catalytic hydrogenolysis in a known manner in the presence of a palladium catalyst, and the amino-protecting tert-butoxycarbonyl group may be removed by mild acidolysis with hydrogen bromide in acetic acid, with trifluoroacetic acid or with hydrogen chloride in an organic solvent.

The compound of the formula (IIIa) where $R_2$ denotes an acyl group, may also be produced by acylating in a known manner a corresponding compound where $R_2$ denotes a hydrogen atom, with an acyl chloride or anhydride which has the acyl group to be introduced as the group $R_2$.

Amongst the new compounds of the formula (III) according to this invention, the new compound of the formula (IIIb) which is in the form of a tri-peptide is produced by a process comprising condensing the naturally occurring bestatin (U.S. Pat. No. 4,029,547), a metabolic product of bestatin or an optical isomer thereof represented by the formula (V):

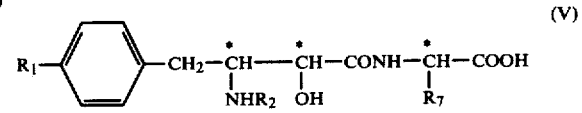

(V)

wherein $R_1$, $R_2$, $R_7$ and the asterisk (*) are as defined hereinbefore in respect of the formula (IIIb), with an amino acid represented by the formula (VI):

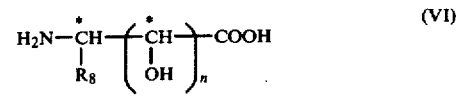

(VI)

wherein $R_8$, n and the asterisk (*) are each as defined hereinbefore in respect of the formula (IIIb) or with a protected derivative of said amino acid (VI) having protected its functional group (e.g. amino group, hydroxyl group, carboxyl group, guanidyl group or mercapto group, if exists) which should not participate in the condensation, in a manner known for the conventional synthesis of peptides, and if required, removing the residual protective group(s) from the resulting condensation product to give the desired product (IIIb).

The starting compound of the formula (V) as employed in the process just mentioned above may be prepared by a method as described in the "Journal of Medicinal Chemistry" Vol. 20, 510–515 (1977). The condensation of the starting compound (V) with the amino acid compound (VI) is performed at a temperature of −20° C. to 25° C. by a known method for synthesis of peptides, for example, according to the carbodiimide method using dicyclohexylcarbodiimide as the condensation agent; according to the active ester method using e.g. hydroxysuccinimide ester, according to the active amide method using imidazole and the like; according to the active azide method using e.g. hydrazine; or according to the mixed acid anhydride method using ethyl chloroformate. The organic solvent in which the condensation is conducted may be those employed for the conventional synthesis of peptides and includes, for example, ethers such as tetrahydrofuran and dioxane; esters such as ethyl acetate; ketones such as acetone; halogenated hydrocarbons such as methylene chloride; amides such as dimethylformamide; and nitriles such as acetonitrile. The protected derivative of the amino acid reagent (VI) may preferably be in the form of the acid-addition salt (for example, p-toluenesulfonate or hydrochloride of a lower alkyl or benzyl ester of the amino acid (VI). When the starting compound (V) is condensed with the amino acid reagent (VI) having blocked its functional group, for example, by the carbodiimide method, the condensation is achieved preferably in the presence of an organic tertiary amine such as N-methylmorpholine, triethylamine and the like. The removal of the residual amino-protecting group from the condensation product may be done by a deprotecting technique known in the chemistry of peptides. For instance, the amino-protecting aralkyloxycarbonyl group, especially benzyl-oxycarbonyl group may be removed by catalytic hydrogenolysis in the presence of a palladium catalyst, and the alkoxycarbonyl group such as tert-butoxycarbonyl group may be removed by mild acidolysis with hydrogen bromide in acetic acid, with trifluoroacetic acid or with hydrogen chloride in an organic solvent such as dioxane, tetrahydrofuran and ethyl acetate.

Further, it is known that 3-amino-2-hydroxy-4-phenylbutanoic acid (abbreviated as AHPA hereinafter) is obtained by hydrolysis of bestatin with hydrochloric acid (see U.S. Pat. No. 4,189,604) and a lower alkyl ester and benzyl ester of AHPA, and amide derivatives of AHPA have been prepared by the present inventors and others.

(2S,3R)-AHPA and its three stereo isomers, namely (2R,3S)-AHPA, (2S,3S)-AHPA and (2R,3R)-AHPA were synthesized by acidolysis of 3-N-benzyloxycarbonylamino-2-hydroxy-4-phenylbutyronitrile, followed by separation procedure as described in U.S. Pat. No. 4,189,604. However, this U.S. patent is silent on the physiological activities of the (2S,3R)-AHPA and the stereo isomers thereof. Only in the "Journal of Medicinal Chemistry" Vol. 20, No. 4, pp. 510-515 (1977), there is described that (2S,3R)-AHPA exhibits a weak inhibitory activity to aminopeptidase B. In the past, no report has been made about whether (2S,3R)-AHPA and the stereo isomers thereof have the immunopotentiating activities, as far as the inventors are aware of.

We have now found that (2S,3R)-AHPA and the stereo isomers thereof as well as some related known compounds thereof, for example, (2S,3R)-AHPA amide and (2S,3R)-3-amino-2-hydroxy-4-p-hydroxyphenylbutanoic acid (abbreviated as (2S,3R)-p-OH-AHPA) which are represented by the general formula (VII):

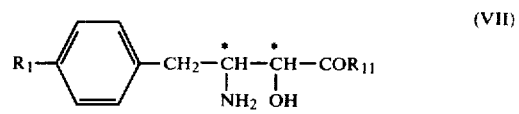

wherein $R_1$ is a hydrogen atom or a hydroxyl group, and $R_{11}$ is a hydroxyl group, an alkoxyl group of 1 to 4 carbon atoms, benzyloxy group or an unsubstituted or substituted amino group, exhibits an immunopotentiating activity which is higher than that of bestatin at a lower dosage.

The alkyl ester and benzyl ester of AHPA as well as the amide derivatives of AHPA may be produced from AHPA by a chemical method as described, for example, in the "Journal of Antibiotics" Vol. 29, No. 5, pp. 600–601 (1976). We have found that when the compound of the formula (VII) is tested by the technique of Delayed Type Hypersensitivity (D.T.H.) using sheep red blood cell as the antigen to be injected subcutaneously into footpad of mouse, it even at a low dosage of 0.01 mcg to 10 mcg/mouse enhances establishment of the D.T.H. response against sheep red blood cell, and hence that the known compound of the formula (VII) is highly active to enhance the cell-mediated immune response.

In consequence, we have now found that the new compound of the general formula (I) and the known compound of the general formula (VII) are useful as the immunopotentiator for enhancing the cell-mediated immune response in living animals including man.

According to a second aspect of this invention, therefore, there is provided a pharmaceutical composition, useful as immunopotentiator, comprising as active ingredient the compound of the formula (VIII):

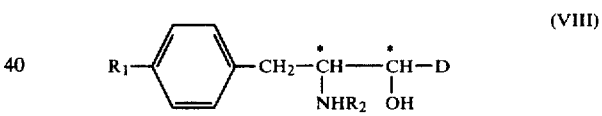

wherein $R_1$ is a hydrogen atom or a hydroxyl group, $R_2$ is a hydrogen atom, an alkanoyl group of 2 to 7 carbon atoms or an alkoxycarbonyl group of 2 to 7 carbon atoms or an aralkyloxycarbonyl group of 7 to 8 carbon atoms, especially benzyloxycarbonyl, and D is the group:

—COOH,
—COOR$_{12}$ where R$_{12}$ is an alkyl of 1 to 4 carbon atoms,

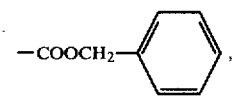

—CONH$_2$,
—CONHR$_{13}$ where R$_{13}$ is an alkyl group of 1 to 4 carbon atoms,
—CH$_2$OH,

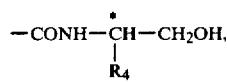

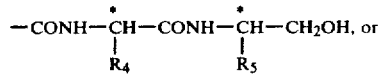

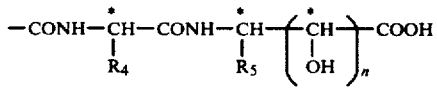

wherein R₄ and R₅ may be the same or different from each other and are each an alkyl group of 1 to 7 carbon atoms, a hydroxyalkyl group of 1 to 7 carbon atoms, a mercaptoalkyl group of 1 to 7 carbon atoms, a carboxamidoalkyl group of 2 to 8 carbon atoms, an aminoalkyl group of 1 to 7 carbon atoms, a guanidyl-N-alkyl group of 2 to 7 carbon atoms, an alkylmercaptoalkyl group of 2 to 7 carbon atoms, a carboxyalkyl group of 2 to 8 carbon atoms, an aryl group, particularly phenyl, an aralkyl group of 7 to 8 carbon atoms, particularly benzyl, or a substituted aralkyl group of 2 to 8 carbon atoms, n is zero or 1, and the asterisk (*) denotes the R-configuration or S-configuration, in combination with a pharmaceutically acceptable carrier for active ingredient.

According to a preferred embodiment of the second aspect of this invention, there is provided a pharmaceutical composition, useful as immunopotentiator, comprising as active ingredient the new compound of the formula (III) shown hereinbefore.

According to a further preferred embodiment of the second aspect of this invention, there is provided a pharmaceutical composition, useful as immunopotentiator, comprising as active ingredient, a compound of the formula (VIIIa):

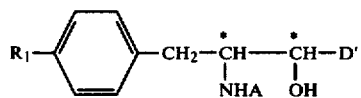
(VIIIa)

wherein R₁ is a hydrogen atom or a hydroxyl group, A is a hydrogen atom or an alkanoyl group of 2 to 5 carbon atoms, especially acetyl, and D' is the group:

—COOH,
—COOR₁₂ where R₁₂ is an alkyl group of 1 to 4 carbon atoms,
—CONH₂,
—CH₂OH,

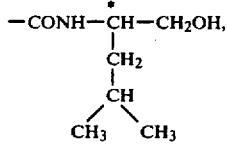

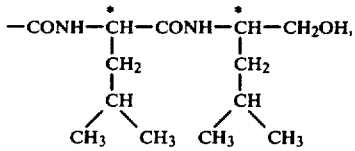

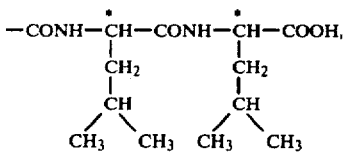

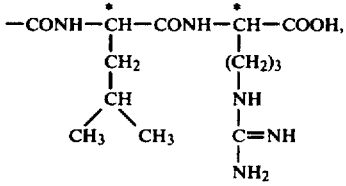

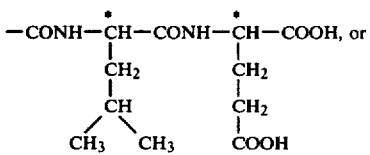

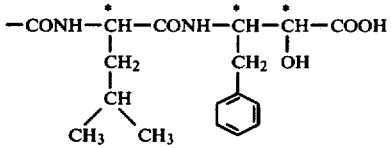

in combination with a pharmaceutically acceptable carrier for the active ingredient.

According to an another aspect of this invention, there is provided a process of potentiating the immune response in a living animal including man, which comprises administering orally, parenterally or intrarectally into the animal an immunopotentiatingly effective amount of the compound of the formula (VIII) or (VIIIa) as described above.

Amongst the new compound of the formula (III), including the new compounds of the formulae (IIIa) and (IIIb) according to this invention, as well as the known compound of the formula (VII) used in this invention, the aforesaid Compound Nos. 1, 2, 3, 4 and 5, as well as the known compounds (2S,3R)-AHPA, (2R,3R)-AHPA, (2S,3R)-AHPA amide and p-OH-AHPA are soluble in water and advantageously can readily be formulated into injectable aqueous solution according to the conventional pharmaceutical technique, whereas the known compound, bestatin is sparingly soluble in water and cannot be formulated into injectable aqueous solution.

In order to estimate the acute toxicity of the compound of the formula (VIII), some of the test compound was interaperitoneally given to ICR-strain mice (in groups each consisting of 6 mice, male, 5 weeks-aged, average body weight 20 g.), when all the tested mice tolerated intraperitoneal administration of (2S,3R)-AHPA; (2S)-2-N-[(2'S,3'R)-3'-amino-2'-hydroxy-4'-phenyl-butanoyl]amino-4-methyl-pentanol; (2S)-2-N-[(2'S,3'R)-3'-amino-2'-hydroxy-4'-phenylbutanoyl-(S)-leucyl]amino-4-methyl-pentanol; (2S,3R)-3-amino-2-hydroxy-4-phenylbutanoyl-(S)-leucyl-(S)-leucine; and (2S,3R)-3-amino-2-hydroxy-4-phenyl-butanoyl-(S)-leucyl-(S)-arginine at a dosage of 100 mg/kg.

The pharmaceutical composition of this invention, owing to its high immunopotentiating activity, may widely be utilized in an immunotherapeutic treatment of tumors and also for an agent of preventing bacterial infections. The composition of this invention may be formulated for oral, parenteral or intrarectal administration. Composition in the form of injectable solution may contain 0.1% to 10.0% by weight of the compound (VIII) or (VIIIa) as active ingredient, and also one or more of a pH-adjuster, buffer, stabilizer, excipient, local anesthetics and an additive for rendering the solution isotonic. The injectable solution may be prepared to be adapted for subcutaneous, intramuscular or intravenous injection by any conventional pharmaceutical technique. Solid composition for oral administration which may be in the form of tablets, coated tablets, granules, powder and capsules, may contain excipients for the active ingredient, and if required, other additives, including disintegrators, lubricants, colorants, flavors and the like. The proportion of the active compound to the carrier may be at a ratio of 1:1 to 1:100 by weight and may usually be chosen appropriately depending on the form of the orally administrable formulation prepared. Suppository formulations may contain excipients and, if necessary, surfactant and lubricants additionally to the active compound.

The optimum dosage of the compound (VIII) or (VIIIa) administered will, of course, depend on the mode of administration and the treatment aimed. For men, the unit dosage generally contains from 0.002 mg to 200 mg of the compound (VIII) or (VIIIa), which may be administered orally in divided doses one or more times per day. The new compound of the formula (IIIa) or (IIIb) used in the composition of this invention may be administered orally to an adult person at a dosage of 50 mg to 200 mg once a day, while the known compound of the formula (VI) used in the composition of this invention may be administered orally to an adult person at a dosage of 0.002 mg to 200 mg once a day, by way of a guideline.

The physiological activities of the compounds according to or used by this invention are tested as follows.

EXAMPLE 1

This Example describes the activity of the compound inhibitory to aminopeptidase B.

The aminopeptidase B-inhibiting activity was determined according to a modification of the method of V. K. Hopsu et al. described in the "Archives of Biochemistry and Biophysics" Vol. 114, 557 (1966). Thus, a mixture of 0.8 ml of 0.1 mM of (S)-arginine $\beta$-naphthylamide and 1.0 ml of 0.1 M Tris-hydrochloride buffer (pH 7.0) was admixed with 0.7 ml of 0.1 M Tris-hydrochloride buffer (pH 7.0) containing the test compound and then heated at 37° C. for 3 minutes. The enzymatic reaction was started by addition of 0.2 ml of an aminopeptidase B solution which had been purified by the chromatographic method of Hopsu et al. with Sephadex G-100 (a product of Pharamcia Fine Chemical Co., Sweden). After the reaction at 37° C. for 30 minutes, the reaction solution was admixed with 0.6 ml of 1.0 M acetate buffer (pH 4.2) containing 1.0 mg/ml of diazonium salt of o-aminoazotoluene (Garnet GBC) and 1.0% of a surfactant "Tween" 20 (a registered trademark) to stop the enzymatic reaction and then allowed to stand at ambient temperature for 15 minutes. After this, absorbance (a) at 525 nm of the reaction solution was measured by spectrophotometer. For the control, the above procedure was repeated without the test compound and the adsorbance (b) was measured. Percentages for inhibition to aminopeptidase B were calculated according to the equation.

$$\text{Inhibition percentages} = \frac{(b - a)}{b} \times 100$$

Inhibition percentages at various concentrations of the test compound were measured, and from the values of inhibition percentages measured 50% Inhibition Concentration ($IC_{50}$) was evaluated. The results are summarized in Table 1 below.

TABLE 1

| Test No. | Test Compounds | $IC_{50}$ (mcg/ml) |
|---|---|---|
| 1 | Compound No. 1 | >50 |
| 2 | Compound No. 2 | 0.65 |
| 3 | Compound No. 3 | 48.9 |
| 4 | Compound No. 4 | 5.4 |
| 5 | Compound No. 5 | 0.11 |
| 6 | Compound No. 6 | 0.20 |
| 7 | Compound No. 7 | 15 |
| 8 | Compound No. 8 | 53 |
| 9 | Bestatin (comparative) | 0.03 |

Notes:
Compound No. 1: (2S,3R)-3-amino-2-hydroxy-4-phenyl-1-butanol-hydrochloride (see Example 6 (b))
Compound No. 2: (2S)-2-N—[(2'S,3'R)-3'-amino-2'-hydroxy-4'-phenylbutanoyl]amino-4-methyl-pentanol (see Example 7 (b))
Compound No. 3: (2S)-2-N—[(2'S,3'R)-3'-N—acetylamino-2'-hydroxy-4'-phenylbutanoyl]amino-4-methyl-pentanol (see Example 8)
Compound No. 4: (2S)-2-N—[(2'S,3'R)-3'-amino-2'-hydroxy-4'-phenylbutanoyl-(S)-leucyl]amino-4-methyl-pentanol (see Example 10 (b))
Compound No. 5: (2S,3R)-3-amino-2-hydroxy-4-phenyl-butanoyl-(S)-leucyl-(S)-arginine (sometimes abbreviated as BST—L—Arg hereinafter, see Example 12 (b))
Compound No. 6: (2S,3R)-3-amino-2-hydroxy-4-phenylbutanoyl-(S)-leucyl-(S)-leucine (sometimes abbreviated as BST—L—Leu hereinafter, see Example 11 (b))
Compound No. 7: (2S,3R)-3-amino-2-hydroxy-4-phenylbutanoyl-(S)-leucyl-(R)-leucine (sometimes abbreviated as BST—D—Leu hereinafter, see Example 13 (b))
Compound No. 8: (3R)-N—[(2'S,3'R)-3'-amino-2'-hydroxy-4'-phenylbutanoyl-(S)-leucyl]amino-(2S)-2-hydroxy-4-phenyl-butanoic acid (sometimes abbreviated as BST—AHPA hereinafter, see Example 15)

EXAMPLE 2

This Example describes the tests for evaluation of the immunopotentiating activity of the new compound of this invention. Thus, the effect of the new compound on cell-mediated immunity was tested according to a known technique of Delayed Type Hypersensitivity (D.T.H.) (see P. H. Lagrange et al. "J. Exp. Med." Vol. 139, 1529–1539 (1974) using mice immunized with sheep red blood cell (SRBC) as antigen which was inoculated into the footpad of mice.

A suspension of $10^8$ sheep red blood cells in 0.05 ml of physiological saline were subcutaneously injected at the time of immunization into the right hind footpad of each $CDF_1$-mouse under test (female, 8 weeks-aged, 5 mice in each group) to establish D.T.H. Simultaneously to the immunization, to the mouse under test was given orally 0.5 mg/kg of the test compound as the solution which was prepared by dissolving the test compound in physiological saline and then filtering the solution by a micropore filter (pore diameter: 0.22 micrometers). Four days later, $10^8$ SRBC were subcutaneously injected into the left hind footpad of each test mouse for elicitation of the D.T.H. response. 24 Hours after the elicitating injection, the increased thickness of the left hind footpad was measured with calipers to estimate the degree of swelling in the footpad. The swelling degree is expressed in term of the values calculatec by the equation:

$$\text{Degree of swelling (\%)} = \frac{\text{Increase in thickness of the left footpad of mouse treated with test compound}}{\text{Increase in thickness of the left footpad of mouse untreated}} \times 100$$

The degree of swelling serves to evaluate the degree of cell-mediated immunity involved. For comparison, a suspension of bestatin dispersed in water was tested in the same way as above. The test results obtained are summarized in Table 2 below.

TABLE 2

| Test Compounds | Dosages (mg/kg) | Degree of swelling (%) |
| --- | --- | --- |
| Compound No. 1 | 0.5 | 129 |
|  | 0.05 | 123 |
| Compound No. 2 | 0.5 | 126 |
|  | 0.05 | 106 |
| Compound No. 3 | 0.5 | 131 |
|  | 0.05 | 124 |
| Compound No. 4 | 0.5 | 103 |
| Compound No. 5 | 0.5 | 135 |
| Compound No. 6 | 0.5 | 120 |
| Compound No. 7 | 0.5 | 120 |
| Compound No. 9 | 5 | 136 |
|  | 0.5 | 109 |
| Bestatin (comparative) | 0.5 | 140–150 |
|  | 0.05 | 120–130 |

Note:
Compound No. 9: (2S,3R)-3-amino-2-hydroxy-4-phenyl-butanoyl-(S)-leucyl-(S)-glutamic acid (see Example 14).

EXAMPLE 3

This Example describes the immunopotentiating activity of the (2S,3R)-AHPA, that is, (2S,3R)-amino-2-hydroxy-4-phenylbutanoic acid amongst the known compounds of the formula (VII) used in this invention.

(A) Effect of (2S,3R)-AHPA on cell-mediated immunity

The effect of (2S,3R)-AHPA on cell-mediated immunity was tested in the same way in Example 2, namely according to the D.T.H. technique using mice immunized with sheep red blood cell as antigen.

Thus, a suspension of $10^8$ sheep red blood cells in 0.05 ml of physiological saline were subcutaneously injected at the time of immunization into the right hind footpad of each $CDF_1$-mouse under test (female, 8 weeks-aged, 5 mice in each group) to establish D.T.H. Simultaneously to this immunization, to the mouse under test was given orally 10 mcg/mouse, 1 mcg/mouse or 0.1 mcg/mouse of the test compound, (2S,3R)-AHPA as the aqueous solution which was prepared by dissolving the test compound in physiological saline and filtering the solution by a micropore filter (pore diameter: 0.22 micrometers). Four days later, $10^8$ SRBC were subcutaneously injected into the left hind footpad of each test mouse for elicitation of the D.T.H. response. 24 Hours after the elicitating injection, the increased thickness of the left hind footpad was measured with calipers to estimate the degree of swelling in the footpad. The degree of swelling was evaluated. The results obtained are listed in Table 3 below. By way of comparison, bestatin was tested in the same way as above. It has been revealed that (2S,3R)-AHPA enhances the D.T.H. response much more than bestatin as long as the dosages of these compounds are lower than 1 mcg/mouse.

TABLE 3

Effect of (2S,3R)-AHPA and bestatin orally administered on establishment of D.T.H. response in mice immunized with SRBC as antigen

| Test Compounds and dosages | Increase in thickness of footpad (×0.1 mm)(±S.D.) | Degree of swelling (%) |
| --- | --- | --- |
| Control | 7.9 ± 1.22 | 100 |
| (2S,3R)-AHPA 10 mcg/mouse | 10.9 ± 0.57 | 138* |
| (2S,3R)-AHPA 1 mcg/mouse | 11.9 ± 0.97 | 151* |
| (2S,3R)-AHPA 0.1 mcg/mouse | 11.6 ± 1.85 | 147* |

TABLE 3-continued

Effect of (2S,3R)-AHPA and bestatin orally administered on establishment of D.T.H. response in mice immunized with SRBC as antigen

| Test Compounds and dosages | Increase in thickness of footpad (×0.1 mm)(±S.D.) | Degree of swelling (%) |
| --- | --- | --- |
| (2S,3R)-AHPA 0.01 mcg/mouse | 10.6 ± 1.17 | 134 |
| Bestatin 10 mcg/mouse | 12.0 ± 1.25 | 152* |
| Bestatin 1 mcg/mouse | 10.3 ± 0.96 | 130* |
| Bestatin 0.1 mcg/mouse | 9.3 ± 2.70 | 118 |

*$p < 0.05$

(B) Effect of (2S,3R)-AHPA given at low dosage on cell-mediated immunity

The effect of (2S,3R)-AHPA on the D.T.H. response was estimated in the same manner as in the above procedure (A) of Example 3 by orally administering 1 mcg/mouse, 0.1 mcg/mouse or 0.01 mcg/mouse of (2S,3R)-AHPA to each mouse under test. The test results obtained are summarized in Table 4 below, from which it will be evident that (2S,3R)-AHPA even at a low dosage of 0.01 mcg/mouse is active to enhance the cell-mediated immunity.

TABLE 4

Effect of (2S,3R)-AHPA and bestatin orally administered at low dosages on establishment of D.T.H. response in mice immunized with SRBC as antigen

| Test Compounds and dosages | Increase in thickness of footpad (×0.1 mm)(±S.D.) | Degree of swelling (%) |
| --- | --- | --- |
| Control | 8.1 ± 1.13 | 100 |
| (2S,3R)-AHPA 1 mcg/mouse | 10.8 ± 1.29 | 133* |
| (2S,3R)-AHPA 0.1 mcg/mouse | 11.1 ± 0.82 | 137* |
| (2S,3R)-AHPA 0.01 mcg/mouse | 10.1 ± 1.52 | 125* |
| Bestatin 1 mcg/mouse | 10.8 ± 1.08 | 133* |

*$p < 0.05$

(C) Effect of mode of administration of (2S,3R)-AHPA on cell-mediated immunity The effect of the mode of administering (2S,3R)-AHPA on the D.T.H. response was estimated in the same manner as in the procedure (A) of Example 3, except that the test compound (as aqueous solution) was injected intraperitoneally in stead of being given orally. The test results obtained are summarized in Table 5 below.

TABLE 5

Effect of (2S,3R)-AHPA orally or intraperitoneally administered on establishment of D.T.H. response in mice immunized with SRBC as antigen

| Test Compounds | Degree of swelling (%) | |
| --- | --- | --- |
|  | Intraperitoneal injection | Oral administration |
| (2S,3R)-AHPA 10 mcg/mouse | 128* | 126* |
| (2S,3R)-AHPA 1 mcg/mouse | 143* | 135* |
| Bestatin 1 mcg/mouse (as aqueous suspension) | 128* | 133* |

*$p < 0.05$

As shown in Table 5, it will be clear that (2S,3R)-AHPA, either upon intraperitoneal injection or upon oral administration, enhances the cell-mediated immunity as much as or much more than bestatin.

As will be clear from the results of the above Tables 3, 4 and 5, upon oral administration, a dosage of (2S,3R)-AHPA in a range of 0.01 to 1 mcg/mouse gives an optimum result in enhancing the D.T.H. response in mice immunized with SRBC as antigen. While, the optimum dosage of bestatin is in a range of 0.1 to 100 mcg per mouse upon oral administration, as described in Japanese patent application unexamined prepublication "Kokai" No. 117435/77.

EXAMPLE 4

Following the procedure (A) of the above Example 3, the immunopotentiating effect of (2R,3S)-AHPA, (2S,3S)-AHPA and (2R,3R)-AHPA which are the stereo isomers of the (2S,3R)-AHPA was estimated by the D.T.H. technique. The test results obtained are shown in Table 6 below.

TABLE 6

Effect of (2S,3S)-AHPA, (2R,3S)-AHPA and (2R,3R)-AHPA orally given on establishment of D.T.H. response in mice immunized with SRBC as antigen

| Test Compounds and dosages | | Increased in thickness of footpad (×0.1 mm)(±S.D.) | Degree of swelling (%) |
|---|---|---|---|
| (2S,3S)-AHPA | 10 mcg/mouse | 11.9 ± 1.36 | 135* |
| (2S,3S)-AHPA | 1 mcg/mouse | 0.8 ± 1.56 | 111 |
| (2R,3S)-AHPA | 10 mcg/mouse | 10.6 ± 0.97 | 120* |
| (2R,3S)-AHPA | 1 mcg/mouse | 11.7 ± 1.15 | 133* |
| (2R,3R)-AHPA | 10 mcg/mouse | 9.6 ± 0.65 | 109 |
| (2R,3R)-AHPA | 1 mcg/mouse | 11.9 ± 0.74 | 135* |

*p < 0.05

EXAMPLE 5

This Example describes the effect of an ester and amide of (2S,3R)-AHPA on cell-mediated immunity.

The effect of the various esters of (2S,3R)-AHPA on the D.T.H. response was estimated in the same manner as in the procedure (A) of Example 3 by orally administering 10 mcg/mouse or 1 mcg/mouse of (2S,3R)-AHPA methylester hydrochloride or (2S,3R)-AHPA amide to each mouse under test. The test results obtained are as listed in Table 7 below, from which it will be evident that the ester of (2S,3R)-AHPA is active substantially as much as the free acid form of (2S,3R)-AHPA to enhance the D.T.H. response and hence the cell-mediated immunity.

TABLE 7

Effect of methyl ester or amide of (2S,3R)-AHPA orally given on establishment of D.T.H. response in mice immunized with SBRC as antigen

| Test Compounds and dosages | | Increase in thickness of footpad (×0.1 mm)(±S.D.) | Degree of swelling (%) |
|---|---|---|---|
| Control | | 8.7 ± 0.65 | 100 |
| (2S,3R)-AHPA methylester hydrochloride | 10 mcg/mouse | 11.5 ± 1.12 | 132* |
| | 1 mcg/mouse | 11.7 ± 1.29 | 134* |
| (2S,3R)-AHPA amide | 10 mcg/mouse | 11.5 ± 1.20 | 131* |
| | 1 mcg/mouse | 9.8 ± 0.82 | 111 |
| (2S,3R)-AHPA | 10 mcg/mouse | 11.0 ± 1.05 | 126* |
| | 1 mcg/mouse | 11.7 ± 1.29 | 135* |
| Bestatin | 1 mcg/mouse | 11.6 ± 0.91 | 133* |

*p < 0.05

Notes:
The (2S,3R)-AHPA amide is the compound of formula

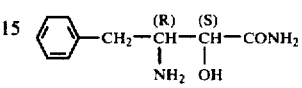

EXAMPLE 6

This Example describes the effect of a substituted derivative of (2S,3R)-AHPA on cell-mediated immunity.

The effect of (2S,3R)-3-amino-2-hydroxy-4-p-hydroxyphenylbutanoic acid ((2S,3R)-p-OH-AHPA) on the D.T.H. response was estimated in the same manner as in the procedure (A) of Example 3 by orally administering 10 mcg/mouse or 1 mcg/mouse of (2S,3R)-p-OH-AHPA to each mouse under test. The test results obtained are summarized in Table 8 below. From the results of Table 8, it will be clear that the tested derivative of (2S,3R)-AHPA at the dosages under test enhances likewise the cell-mediated immunity.

TABLE 8

Effect of the hydroxylated derivative of (2S,3R)-AHPA on establishment of D.T.H. in mice immunized with SRBC as antigen

| Test Compounds and dosages | | Increase in thickness of footpad (×0.1 mm)(±S.D.) | Degree of swelling (%) |
|---|---|---|---|
| (2S,3R)-p-OH—AHPA | 10 mcg/mouse | 11.0 ± 1.75 | 129* |
| | 1 mcg/mouse | 9.7 ± 0.54 | 114* |
| Bestatin (comparative) | 1 mcg/mouse | 10.3 ± 1.36 | 121* |
| Control | | 8.5 ± 0.44 | 100 |

*p < 0.05

From the results of Examples 3, 4, 5 and 6 as above, it will be clear that (2S,3R)-AHPA and some derivatives thereof as given at a low dosage are active to enhance significantly the cell-mediated immunity, and also that (2S,3R)-AHPA given orally at a dosage of 0.01 to 10 mcg/mouse exhibits the immunopotentiating activity as high as bestatin orally given at a dosage of 1 to 10 mcg/mouse, as measured according to the D.T.H. response in mice immunized with SRBC as antigen.

The following Examples 7-16 illustrate the synthetic procedure for the production of the new compounds of this invention accordance to the formula (IIIa).

EXAMPLE 7

(a) Synthesis of (2S,3R)-3-N-t-butoxycarbonylamino-2-hydroxy-4-phenyl-1-butanol

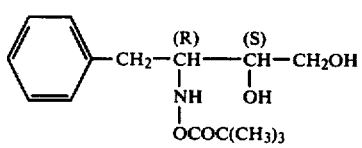

N-t-Butoxycarbonyl-(2S,3R)-3-amino-2-hydroxy-4-phenylbutanoic acid methylester (92.8 mg) was dissolved in 0.44 ml of ethanol, and to the resultant solution was added dropwise at ambient temperature 2.3 ml of ethyl alcohol containing 46.6 mg of sodium borohydride. After this, the mixture was stirred for 2 hours at ambient temperature to effect the reduction of the carboxylate group. After the reaction was completed, the reaction mixture was concentrated to dryness under reduced pressure and the solid residue was taken up into 3 ml of ethyl acetate. The solution obtained was washed with 2 ml of an aqueous solution of 1% citric acid and then with three 2 ml portions of saturated aqueous sodium chloride. The organic solvent phase in the ethyl acetate was dried over magnesium sulfate for the drying purpose, and the mixture was filtered to remove the magnesium sulfate hydrate therefrom. The filtrate was concentrated to dryness to give 81 mg of a crude solid of the titled compound. When this was recrystallized from a mixture of 0.5 ml of ethylether and 0.5 ml of n-hexane, there was obtained 68 mg of colorless needles. m.p. 113°-115° C. This product gave a value of m/e 282 (M+1) in the analysis of mass spectrometry.

Elemental analysis— Found: C, 63.69; H, 8.31; N, 4.70%. Calcd. for $C_{15}H_{23}NO_4$ (molecular weight 281.39): C, 64.00; H, 8.26; N, 4.98%.

(b) Synthesis of (2S,3R)-3-amino-2-hydroxy-4-phenyl-1-butanol hydrochloride

The compound (68 mg) obtained in the above step (a) was dissolved in 0.4 ml of dry methanol containing 20% hydrogen chloride under ice-cooling and then allowed to stand for 30 minutes to effect removal of the t-butoxycarbonyl group. The reaction mixture was then concentrated to dryness and the residue was recrystallized from ethanol-ethylether to afford 36 mg of the titled compound as colorless plate-like crystals. m.p. 123°-125° C. $[\alpha]_D^{25}+28.4°$ (c 1.0, 1 N-HCl). This product gave a value of m/e 182 in the analysis of mass spectrometry.

Elemental analysis— Found: C, 54.93; H, 7.46; N, 6.40; Cl, 16.0%. Calcd. for $C_{10}H_{16}NO_2Cl$ (molecular weight 217.72): C, 55.30; H, 7.42; N, 6.44; Cl, 16.3%.

EXAMPLE 8

(a) Synthesis of (2S)-2-N-[(2'S,3'R)-3'-N-t-butoxycarbonylamino-2'-hydroxy-4'-phenylbutanoyl]amino-4-methylpentanol

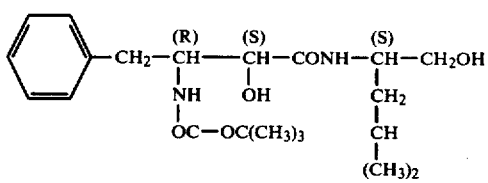

(2S,3R)-3-N-t-Butoxycarbonylamino-2-hydroxy-4-phenylbutanoyl-(S)-leucine methylester (440 mg) was dissolved in a mixture of 8 ml of ethanol and 8 ml of distilled water, and the resulting solution was treated with sodium borohydride in the same manner as in the step (a) of Example 7 for the reduction. The crude product so obtained (347 mg) was recrystallized from ethyl acetate-ethylether to afford 230 mg of the titled compound as colorless needles. m.p. 159.5°-160° C. Mass spectrometry: m/e 394 (M+1).

Elemental analysis— Found: C, 63.92; H, 8.76; N, 7.14%. Calcd. for $C_{21}H_{34}N_2O_5$ (molecular weight 394.57): C, 63.92; H, 8.70; N, 7.10%.

(b) Synthesis of (2S)-2-N-[(2'S,3'R)-3'-amino-2'-hydroxy-4'-phenylbutanoyl]amino-4-methyl-pentanol The compound (300 mg) obtained in the above step (a) was dissolved in 3 ml of dry methanol containing 20% hydrogen chloride and 1.0% anisole under ice-cooling and then allowed to stand for 30 minutes to effect removal of the t-butoxycarbonyl group. The reaction mixture was concentrated to dryness to give 210 mg of the hydrochloride of the titled compound which was hygroscopic and gave a value of m/e 295 in the analysis of mass spectrometry. This hydrochloride was taken up in a volume of water and neutralized with aqueous sodium hydrogen carbonate, and the resulting aqueous solution was extracted with n-butanol. The extract in n-butanol was washed with water and concentrated to dryness to give the free base form of the titled compound as an oil. This oil product gave a value of m/e 295 (M+1) in mass spectrometry and its chemical structure was confirmed with reference to the data of IR. and NMR. $[\alpha]_D^{25}-2.5°$ (c 1.0, 1 N-HCl).

EXAMPLE 9

Synthesis of (2S)-2-N-[(2'S,3'R)-3'-N-acetylamino-2'-hydroxy-4'-phenylbutanoyl]amino-4-methyl-pentanol The compound (42 mg) in the form of the free base obtained in the step (b) of Example 8 as above was dissolved in 0.4 ml of methanol and the solution obtained was admixed with 0.16 ml of acetic anhydride, followed by allowing to stand at ambient temperature overnight to effect acetylation of the amino group of said compound. The reaction solution was concentrated to dryness and the residue was taken up into 2 ml of n-butanol. The solution in n-butanol was washed with 2 ml of water, then with 2 ml of saturated aqueous sodium hydrogen carbonate and finally with water and subsequently concentrated to dryness to give 32 mg of a crude solid of the titled compound. Recrystallization from ethanol-ethylether gave 20 mg of colorless needles. m.p. 188°-189° C. Mass spectrometry: m/e 336 (M+).

Elemental analysis— Found: C, 64.14; H, 8.35; N, 8.30%. Calcd. for $C_{18}H_{28}N_2O_4$ (molecular weight 336.48): C, 64.25; H, 8.40; N, 8.33%.

EXAMPLE 10

Synthesis of (2S)-2-N-[(2'S,3'R)-3'-N-acetylamino-2'-hydroxy-4'-phenylbutanoyl]amino-4-methyl-pentanol (2S,3R)-3-N-Acetylamino-2-hydroxy-4-phenylbutanoyl-(S)-leucine methylester (36.4 mg) was reduced with 16 mg of sodium borohydride and then isolated in the same manner as in the step (a) of Example 8 to afford 20.1 mg of the titled compound. m.p. 187.5°-189° C.

EXAMPLE 11

(a) Synthesis of (2S)-2-N-[(2'S,3'R)-3'-N-benzyloxycarbonylamino-2'-hydroxy-4'-phenylbutanoyl-(S)-leucyl]amino-4-methyl-pentanol

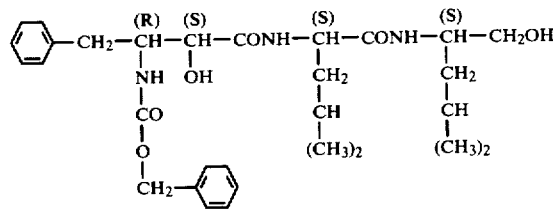

(2'S,3'R)-3'-N-Benzyloxycarbonylamino-2'-hydroxy-4'-phenylbutanoyl-(S)-leucyl-(S)-leucine benzylester (120 mg) was reduced with 38 mg of sodium borohydride and then isolated in the same manner as in the step (a) of Example 7 to give 100 mg of the titled compound as a colorless powder. Mass spectrometry: m/e 528 (M+1).

Elemental ayalysis— Found: C, 67.98; H, 8.03; N, 5.09%. Calcd. for $C_{30}H_{43}N_2O_6$ (molecular weight 527.75): C, 68.27; H, 8.23; N, 5.31%.

(b) Synthesis of (2S)-2-N-[(2'S,3'R)-3'-amino-2'-hydroxy-4'-phenylbutanoyl-(S)-leucyl]amino-4-methyl-pentanol The compound (100 mg) obtained in the step (a) of this Example was dissolved in a mixture of 1 ml of methanol and 0.3 ml of distilled water, and the solution was admixed with 20 mg of palladium black as the catalyst and then subjected to hydrogenolysis at ambient temperature with hydrogen gas at 3 atm. overnight. The reaction mixture was filtered to remove the catalyst and the filtrate was concentrated to give a syrup. This syrup was admixed with 2 ml of ethyl acetate and 3 ml of 1 N hydrochloric acid, and the admixture obtained was extracted with water to transfer the desired deprotected product into the water. The aqueous extract was concentrated to dryness to give 26 mg of the titled compound as a colorless powder. m.p. 78°-80° C. Mass spectrometry: m/e 408.

The following Examples 12-16 illustrate the preparation of the new compounds of this invention according to the formula (IIIb).

EXAMPLE 12

(a) Synthesis of (2S,3R)-3-N-benzyloxycarbonylamino-2-hydroxy-4-phenylbutanoyl-(S)-leucyl-(S)-leucine benzylester

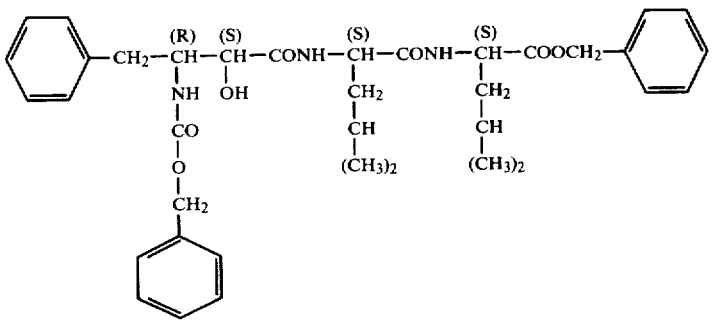

(2S,3R)-3-N-benzyloxycarbonylamino-2-hydroxy-4-phenylbutanoyl-(S)-leucine (442 mg) and (S)-leucine benzylester p-toluenesulfonate (393.3 mg) were admixed with 1 ml of tetrahydrofuran, followed by addition of 0.11 ml of N-methylmorpholine and 115 mg of N-hydroxysuccinimide. The resulting solution was ice-cooled and then admixed with 227 mg of dicyclohexylcarbodiimide, followed by stirring for 4 hours under ice-cooling. The reaction mixture was filtered to remove the urea derivative as produced, and the filtrate was concentrated to dryness under reduced pressure. The solid residue was dissolved in 5 ml of ethyl acetate and the solution obtained was washed with 3 ml of 1 N hydrochloric acid, 3 ml of 1 N aqueous sodium hydroxide and finally with 3 ml of distilled water. The organic solvent phase was mixed with anhydrous magnesium sulfate for drying and then the mixture was filtered to remove the magnesium sulfate hydrate. The solution (the filtrate) was concentrated to dryness under reduced pressure to give 573 mg of a crude solid of the titled compound. Crystallization of this product from acetone-ethylether gave 444 mg of colorless needles. Mass spectrometry of this pure product gave a value of m/e 646 (M+1). The chemical structure of the product was confirmed with reference to the data of IR. and NMR.

Elemental analysis— Found: C, 68.64; H, 6.97; N, 6.30%. Calcd. for $C_{37}H_{47}N_3O_7$ (molecular weight: 645.87): C, 68.80; H, 6.89; N, 6.51%.

(b) Synthesis of (2S,3R)-3-amino-2-hydroxy-4-phenylbutanoyl-(S)-leucyl-(S)-leucine The compound (200 mg) obtained in the above step (a) was taken up into a mixture of 10 ml of dioxane and 0.2 ml of distilled water, and the resultant solution was admixed with 60 mg of palladium black as the hydrogenolysis catalyst. The mixture was subjected to the hydrogenolysis at ambient temperature with hydrogen gas at 3 atm. for 48 hours to effect removal of both the amino-portecting benzyloxycarbonyl group and the carboxyl-protecting benzyl group. The reaction mixture was filtered to remove the catalyst, and the filtrate was concentrated to dryness under reduced pressure. Recrystallization of the solid residue from methanol-ethyl acetate gave 96.8 mg of the titled compound as colorless needles. m.p. 216°-219° C. (with foaming). $[\alpha]_D^{25} -37.0°$ (c 1.0, 1 N-HCl). Mass spectrometry: m/e 422 (M+1).

Elemental analysis— Found: C, 62.89; H, 8.19; N, 9.68%. Calcd. for $C_{22}H_{35}N_3O_5$ (molecular weight: 421.60): C, 62.91; H, 8.39; N, 9.97%.

EXAMPLE 13

(a) Synthesis of (2S,3R)-3-N-benzyloxycarbonylamino-2-hydroxy-4-phenylbutanoyl-(S)-leucyl-(S)-N^G-nitroarginine benzylester

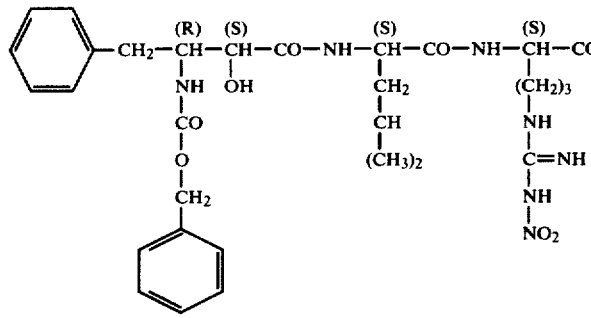

(2S,3R)-3-N-Benzyloxycarbonylamino-2-hydroxy-4-phenylbutanoyl-(S)-leucine (88.4 mg) and N^G-nitroarginine benzylester di-p-toluene-sulfonate (130.8 mg) were dissolved in 1 ml of tetrahydrofuran, followed by addition of 0.022 ml of N-methylmorpholine and 34 mg of N-hydroxysuccinimide thereto. The resulting solution was ice-cooled and admixed with 84 mg of dicyclohexylcarbodiimide, followed by stirring for 24 hours under ice-cooling. The reaction mixture was filtered to remove therefrom the urea derivative as produced. The filtrate was concentrated to dryness and the solid residue was dissolved in 5 ml of ethyl acetate. The solution was washed with 5 ml of 1 N hydrochloric acid 5 ml of 1 N aqueous sodium hydroxide and then 5 ml of distilled water and subsequently mixed with anhydrous magnesium sulfate for drying. The magnesium sulfate hydrate was filtered off and the filtrate was concentrated to dryness to give 142 mg of the titled compound as a powder. Mass spectrometry of this product gave a value of m/e 734 (M+1), and its chemical structure was confirmed with reference to the data of IR. and NMR.

(b) Synthesis of (2S,3R)-3-amino-2-hydroxy-4-phenylbutanoyl-(S)-leucyl-(S)-arginine The compound (117 mg) obtained in the above step (a) was admixed with a mixture of 2.5 ml of dioxane, 0.25 ml of distilled water and 0.25 ml of glacial acetic acid followed by addition of 25 mg of palladium black thereto. The mixture was subjected to hydrogenolysis at ambient temperature with hydrogen gas at 3 atm. for 72 hours, and the reaction mixture was filtered to remove the catalyst. The filtrate was concentrated and the concentrated solution was mixed with a small volume of distilled water and adjusted to pH 2.0 by addition of 6 N hydrochloric acid. The acidified solution was passed through a column of 100 mg of active carbon for chromatography (a product of Wako Junyaku Co., Japan) for adsorption of the desired product. For the purification purpose, the carbon column was developed with distilled water and the eluate was concentrated to dryness to give 156 mg of the purified product as a powder. m.p. 147°-152° C. $[\alpha]_D^{25} -23.5°$ (c, 1 N-HCl). Mass spectrometry: m/e 465. This product showed a positive reaction to Sakaguchi reagent.

EXAMPLE 14

Synthesis of (2S,3)-3-amino-2-hydroxy-4-phenylbutanoyl-(S)-leucyl-(R)-leucine (2S,3R)-3-N-Benzyloxycarbonylamino-2-hydroxy-4-phenylbutanoyl-(S)-leucine (1.11 g) was reacted with 983.3 mg of (R)-leucine benzylester p-toluenesulfonate and the resulting condensation product was isolated in the same manner as in the step (a) of Example 12 to give 1.39 g of the 3-N-benzyloxycarbonyl-protected derivative of (2S,3R)-3-amino-2-hydroxy-4-phenylbutanoyl-(S)-leucyl-(R)-leucine as a powder. This protected product showed a value of m/e 646 in the analysis of mass spectrometry.

This protected product was subjected to the hydrogenolysis with hydrogen over palladium black in the same manner as in the step (b) of Example 12 for the deprotection to give a crude powder of the titled compound. Recrystallization of this powder from methanol gave 510 g of colorless plate-like crystals. m.p. 240°-243° C. Mass spectrometry: m/e 422. When this product was subjected to a silica gel thin layer chromatography on a silica gel plate (Art. 5715, a product of Merck Co., Germany) developed with a mixed solvent of butyl acetate-n-butanol-acetic acid-water (4:4:1:1 by volume), it showed an Rf value of 0.33. While, the isomer product of the Example 12 (b) showed an Rf value of 0.39 in the same silica gel thin layer chromatography as above.

Elemental analysis—Found: C, 63.10, H, 8.09; N, 9.70%. Calcd. for $C_{22}H_{35}N_3O_5$: C, 62.91; H, 8.39; N, 9.97%.

EXAMPLE 15

Synthesis of (2S,3R)-3-amino-2-hydroxy-4-phenylbutanoyl-(S)-leucyl-(S)-glutamic acid

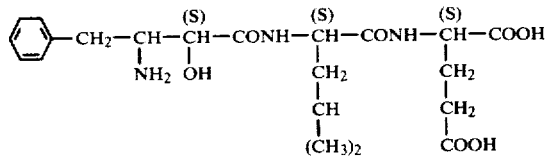

(2S,3R)-3-N-Benzyloxycarbonylamino-2-hydroxy-4-phenylbutanoyl-(S)-leucine (442 mg) was reacted with 500 mg of (S)-glutamic acid benzylester p-toluenesulfonate and the resulting condensation product was isolated in the same manner as in the step (a) of Example 12 to give 667 mg of the 3-N-benzyloxycarbonyl-protected derivative of (2S,3R)-3-N-amino-2-hydroxy-4-phenylbutanoyl-(S)-leucyl-(S)-glutamic acid which gave a value of m/e 662 (M+1) in the analysis of mass spectrometry. This protected product (200 mg) was subjected to hydrogenolysis in the same manner as in the step (b) of Example 12 of the deprotection to give 73 mg of the titled compound as a colorless powder. m.p. 143°–146° C. $[\alpha]_D^{25}$ −24.7° (c 1.0, 1 N-HCl). Mass spectrometry: m/e 438 (M+1).

Elemental analysis—Found C, 57.21, H, 7.31, N, 9.30%. Calcd. for $C_{21}H_{31}N_3O_7$: C, 57.64, H, 7.16, N, 9.61%.

EXAMPLE 16

Synthesis of (3R)-N-[(2'S, 3'R)-3'-amino-2'-hydroxy-4'-phenylbutanoyl-(S)-leucyl]amino-(2S)-2-hydroxy-4-phenylbutanoic acid

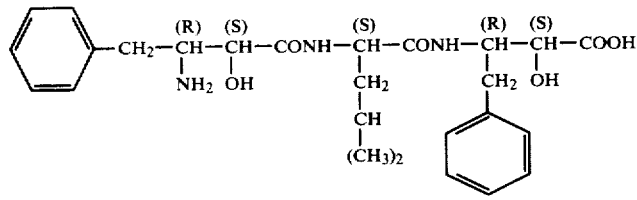

(2S,3R)-3-N-Benzyloxycarbonylamino-2-hydroxy-4-phenylbutanoyl-(S)-leucine (309 mg) was reacted with (2S,3R)-3-amino-2-hydroxy-4-phenylbutyric acid benzylester hydrochloride (225 mg) and the resulting condensation product was isolated in the same manner as in the step (a) of Example 12 to give 440 mg of the 3-N-benzyloxycarbonyl-protected derivative of (3R)-N-[(2'S,3'R)-B 3'-amino-2'-hydroxy-4-phenylbutanoyl-(S)-leucyl] amino-(2S)-2-hydroxy-4-phenylbutanoic acid as colorless needles. m.p. 152°–154° C. Mass spectrometry: m/e 710 (M+1).

This N-protected product (100 mg) was subjected to hydrogenolysis in the same manner as in the step (b) of Example 12 for the deprotection to give 67 mg of a crude powder of the titled compound. Recrystallization from methanol-ethyl acetate gave 42 mg of colorless needles. m.p. 217°–218° C. $[\alpha]_D^{25}$ +17.0° (c 1.0, 1 N-HCl). Mass spectrometry: m/e 486 (M+1).

Elemental analysis—Found: C, 64.20, H, 7.33, N, 8.51%. Calcd. for $C_{26}H_{35}N_3O_6$ (molecular weight 485.64): C, 64.30; H, 7.28; N, 8.66%.

The following Examples 17–19 illustrate the formulation of the pharmaceutical composition of this invention.

EXAMPLE 17

(2S,3R)-Amino-2-hydroxy-4-phenylbutanoic acid i.e., (2S,3R)-AHPA (0.1 g) and mannitol (5 g) were taken up into distilled water to a total volume of 1000 ml, and the solution obtained was sterillized in a conventional manner. The sterillized solution in 2 ml-portions was placed in virales of glass and then freeze-dried. For use, the lyophilized product was dissolved in sterile distilled water to make up an injectable solution.

EXAMPLE 18

One part by weight of (2S,3R)-AHPA was well mixed with 2000 parts by weight of lactose, and the mixture was passed through a 50 mesh screen to give a powdery formulation.

EXAMPLE 19

One part by weight of (2S,3R)-AHPA, 770 parts of lactose, 200 parts of corn starch and 30 parts of polyvinylpyrrolidone (as binder) were well mixed together. The mixture was wetted with a volume of ethanol and granulated. The granules were mixed with 0.5 parts of finely divided magnesium stearate as the lubricant and compressed into the form of tablets each weighing 1 mg.

What we claim is:

1. A new compound of the general formula (III)

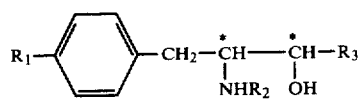

wherein $R_1$ is a hydrogen atom or a hydroxyl group, $R_2$ is a hydrogen atom or an alkanoyl group of 2-7 carbon atoms or an alkoxycarbonyl group of 2-7 carbon atoms, and $R_3$ is selected from the groups:

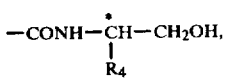

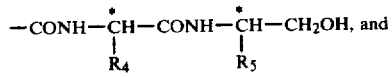

-continued

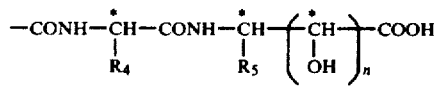

where $R_4$ and $R_5$ may be the same or different from each other and each is an alkyl group of 1–7 carbon atoms, a hydroxyalkyl group of 1–7 carbon atoms, a mercaptoalkyl group of 1–7 carbon atoms, a carboxamidoalkyl group of 2–8 carbon atoms, an aminoalkyl group of 1–7 carbon atoms, a guanidyl-N-alkyl group of 1–7 carbon atoms, an alkylmercaptoalkyl group of 2–7 carbon atoms, a carboxyalkyl group of 2–8 carbon atoms, an aryl group, particularly phenyl, an aralkyl group of 7–8 carbon atoms or a substituted aralkyl group of 7–8 carbon atoms, n is zero or 1, and the asterisk (*) denotes the R-configuration or S-configuration or a combination thereof.

2. A new compound of the formula

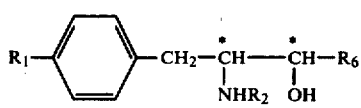

wherein $R_1$ is a hydrogen atom or a hydroxyl group, $R_2$ is a hydrogen atom or an alkanoyl group of 2 to 7 carbon atoms or an alkoxycarbonyl group of 2 to 7 carbon atoms, and $R_6$ is the group:

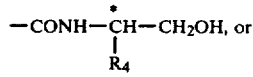

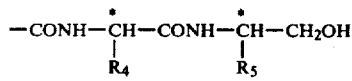

wherein $R_4$ and $R_5$ are as defined in claim 1.

3. A new compound of the formula

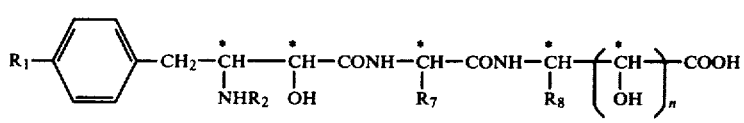

wherein $R_1$ is a hydrogen atom or a hydroxyl group, $R_2$ is a hydrogen atom or an alkanoyl group of 2 to 7 carbon atoms or an alkoxycarbonyl group of 2 to 7 carbon atoms, and $R_7$ and $R_8$ may be the same or different from each other and each is an alkyl group of 1 to 7 carbon atoms, a hydroxyalkyl group of 1 to 7 carbon atoms, a mercaptoalkyl group of 1 to 7 carbon atoms, an aminoalkyl group of 1 to 7 carbon atoms, a guanidyl-N-alkyl group of 1 to 7 carbon atoms, an alkylmercaptoalkyl group, a carboxyalkyl group of 2 to 8 carbon atoms, a carboxamidoalkyl group of 2 to 8 carbon atoms, an aryl group, particularly phenyl group, an aralkyl group, particularly a phenyl ($C_1$–$C_4$) alkyl group, especially benzyl, or a substituted aralkyl group, and n is 0 or 1, and the asterisk (*) each denotes the R-configuration or S-configuration.

4. A new compound of the formula

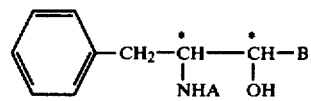

wherein A is a hydrogen atom or an alkanoyl group of 2 to 5 carbon atoms, especially acetyl and B is the group:

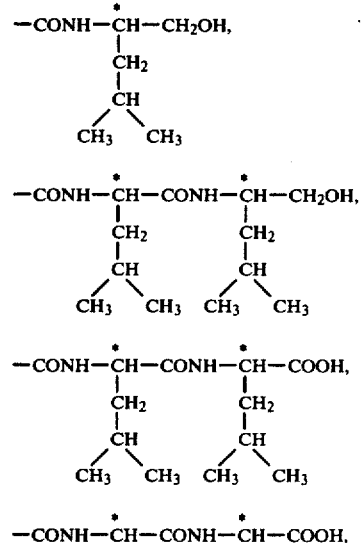

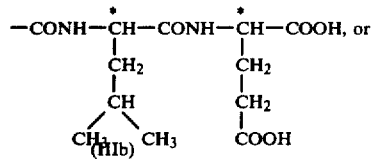

5. The compound of claim 2 which is selected from:
((2S)-2-N-[(2′S,3′R)-3′-amino-2′-hydroxy-4′-phenylbutanoyl]amino-4-methyl-pentanol,
(2S)-2-N-[(2′S,3′R)-3′-N-acetylamino-2′-hydroxy-4′-phenylbutanoyl]amino-4-methyl-pentanol, and
(2S)-2-N-[(2′S,3′R)-3′-amino-2′-hydroxy-4′-phenylbutanoyl-(S)-leucyl]amino-4-methyl-pentanol.

6. The compound of claim 3 which is selected from:

(2S,3R)-3-amino-2-hydroxy-4-phenylbutanoyl-(S)-leucyl-(S)-leucine,
(2S,3R)-3-amino-2-hydroxy-4-phenylbutanoyl-(S)-leucyl-(S)-arginine,
(2S,3R)-3-amino-2-hydroxy-4-phenylbutanoyl-(S)-leucyl-(R)-leucine,
(2S,3R)-3-amino-2-hydroxy-4-phenylbutanoyl-(S)-leucyl-(S)-glutamic acid, and
(3R)-N-[(2'S,3'R)-3'-amino-2'-hydroxy-4'-phenylbutanoyl-(S)-leucyl]amino-(2S)-2-hydroxy-4-phenylbutanoic acid.

7. A pharmaceutical immunopotentiating composition, comprising as active ingredient the compound of the formula (VIII)

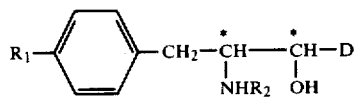

(VIII)

wherein $R_1$ is a hydrogen atom or a hydroxyl group, $R_2$ is a hydrogen atom, an alkanoyl group of 2 to 7 carbon atoms or an alkoxycarbonyl group of 2 to 7 carbon atoms or an aralkyloxycarbonyl group of 7 to 8 carbon atoms, especially benzyloxycarbonyl, and D is the group:

—COOH,
—COOR$_{12}$ where R$_{12}$ is an alkyl of 1 to 4 carbon atoms,

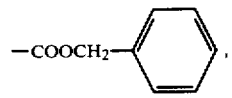

—CONH$_2$,
—CONHR$_{13}$ where R$_{13}$ is an alkyl group of 1 to 4 carbon atoms,
—CH$_2$OH,

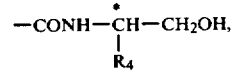

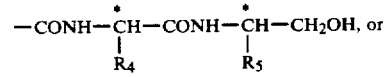

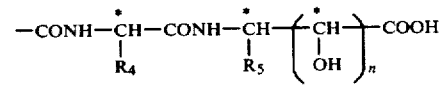

wherein R$_4$ and R$_5$ may be the same or different from each other and each are an alkyl group of 1 to 7 carbon atoms, a hydroxyalkyl group of 1 to 7 carbon atoms, a mercaptoalkyl group of 1 to 7 carbon atoms, a carboxamidoalkyl group of 2 to 8 carbon atoms, an aminoalkyl group of 1 to 7 carbon atoms, a guanidyl-N-alkyl group of 2 to 7 carbon atoms, an alkylmercaptoalkyl group of 2 to 7 carbon atoms, a carboxyalkyl group of 2 to 8 carbon atoms, an aryl group, particularly phenyl, an aralkyl group of 7 to 8 carbon atoms, particularly benzyl, or a substituted aralkyl group of 2 to 8 carbon atoms, n is zero or 1, and the asterisk (*) denotes the R-configuration or S-configuration, in combination with a pharmaceutically acceptable carrier for the active ingredient.

8. The pharmaceutical composition of claim 7, comprising as active ingredient a compound of the formula (VIIIa)

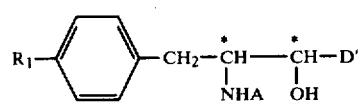

(VIIIa)

wherein $R_1$ is a hydrogen atom or a hydroxyl group, A is a hydrogen atom or an alkanoyl group of 2 to 5 carbon atoms, especially acetyl, and D' is the group:

—COOH,
—COOR$_{12}$ where R$_{12}$ is an alkyl group of 1 to 4 carbon atoms,
—CONH$_2$,
—CH$_2$OH,

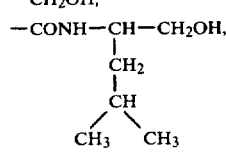

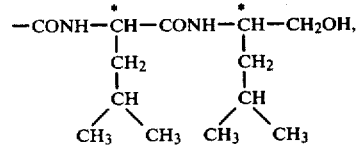

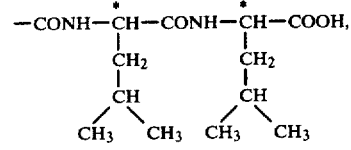

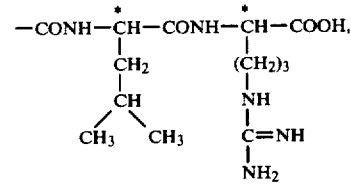

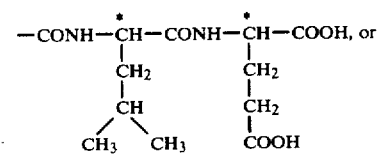

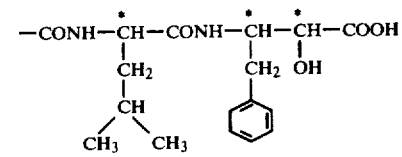

in combination with a pharmaceutically acceptable carrier for the active ingredient.

9. The pharmaceutical composition of claim 7, comprising as active ingredient the new compound of the formula (III)

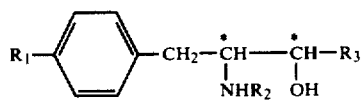  (III)

wherein $R_1$ is a hydrogen atom or a hydroxyl group, $R_2$ is a hydrogen atom or an alkanoyl group of 2–7 carbon atoms or an alkoxycarbonyl group of 2–7 carbon atoms, and $R_3$ is selected from the groups:

—CH$_2$OH,

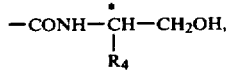

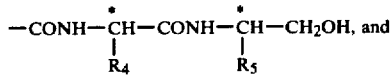

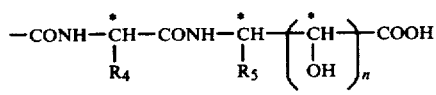

where $R_4$ and $R_5$ may be the same or different from each other and each is an alkyl group of 1–7 carbon atoms, a hydroxyalkyl group of 1–7 carbon atoms, a mercaptoalkyl group of 1–7 carbon atoms, a carboxamidoalkyl group of 2–8 carbon atoms, an aminoalkyl group of 1–7 carbon atoms, a guanidyl-N-alkyl group of 1–7 carbon atoms, an alkylmercaptoalkyl group of 2–7 carbon atoms, a carboxyalkyl group of 2–8 carbon atoms, an aryl group, particularly phenyl, an aralkyl group of 7–8 carbon atoms or a substituted aralkyl group of 7–8 carbon atoms, n is zero or 1, and the asterisk (*) denotes the R-configuration or S-configuration.

10. A process of potentiating the immune response in a living animal including man, which comprises administering orally or parenterally or intrarectally into the animal an immunopotentiatingly effective amount of the compound of the formula (VIII)

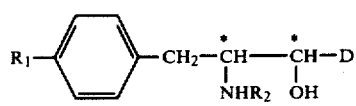  (VIII)

wherein $R_1$ is a hydrogen atom or a hydroxyl group, $R_2$ is a hydrogen atom, an alkanoyl group of 2 to 7 carbon atoms or an alkoxycarbonyl group of 2 to 7 carbon atoms or an aralkyloxycarbonyl group of 7 to 8 carbon atoms, especially benzyloxycarbonyl, and D is the group:

—COOH,
—COOR$_{12}$ where $R_{12}$ is an alkyl of 1 to 4 carbon atoms,

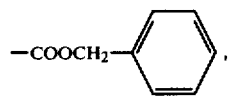

—CONH$_2$,
—CONHR$_{13}$ where $R_{13}$ is an alkyl group of 1 to 4 carbon atoms,
—CH$_2$OH, -continued

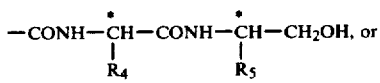

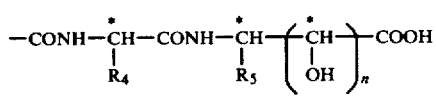

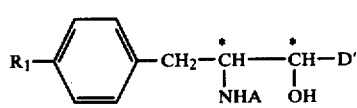

wherein $R_4$ and $R_5$ may be the same or different from each other and each are an alkyl group of 1 to 7 carbon atoms, a hydroxyalkyl group of 1 to 7 carbon atoms, a mercaptoalkyl group of 1 to 7 carbon atoms, a carboxamidoalkyl group of 2 to 8 carbon atoms, an aminoalkyl group of 1 to 7 carbon atoms, a guanidyl-N-alkyl group of 2 to 7 carbon atoms, an alkylmercaptoalkyl group of 2 to 7 carbon atoms, a carboxyalkyl group of 2 to 8 carbon atoms, an aryl group, particularly phenyl, an aralkyl group of 7 to 8 carbon atoms, particularly benzyl, or a substituted aralkyl group of 2 to 8 carbon atoms, n is zero or 1, and the asterisk (*) denotes the R-configuration or S-configuration, in combination with a pharmaceutically acceptable carrier for the active ingredient, or of the compound of the formula (VIIIa):

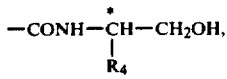  (VIIIa)

wherein $R_1$ is a hydrogen atom or a hydroxyl group, A is a hydrogen atom or an alkanoyl group of 2 to 5 carbon atoms, especially acetyl, and D' is the group:

—COOH,
—COOR$_{12}$ where $R_{12}$ is an alkyl group of 1 to 4 carbon atoms,
—CONH$_2$,
—CH$_2$OH,

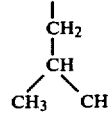

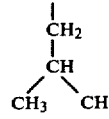

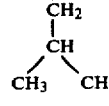

-continued
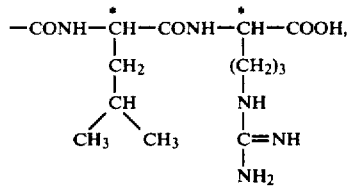
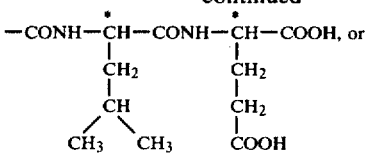
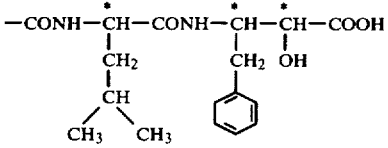
in combination with a pharmaceutically acceptable carrier for the active ingredient.
11. (2S, 3R)-3-amino-2-hydroxy-4-phenylbutanoyl-(S)-leucyl-(S)-leucine.
12. (2S, 3R)-3-amino-2-hydroxy-4-phenylbutanoyl-(S)-leucyl-(S)-arginine.
* * * * *